United States Patent
Valentine et al.

(10) Patent No.: US 11,717,276 B2
(45) Date of Patent: Aug. 8, 2023

(54) SURGICAL DEVICES INCLUDING ADAPTERS AND SEALS

(71) Applicant: Covidien LP, Mansfield, MA (US)

(72) Inventors: David Valentine, Hamden, CT (US); Joseph Eisinger, Northford, CT (US)

(73) Assignee: Covidien LP, Mansfield, MA (US)

( * ) Notice: Subject to any disclaimer, the term of this patent is extended or adjusted under 35 U.S.C. 154(b) by 829 days.

(21) Appl. No.: 16/566,955

(22) Filed: Sep. 11, 2019

(65) Prior Publication Data

US 2020/0129163 A1  Apr. 30, 2020

Related U.S. Application Data

(60) Provisional application No. 62/752,550, filed on Oct. 30, 2018.

(51) Int. Cl.
*A61B 17/00* (2006.01)
*A61B 17/115* (2006.01)

(52) U.S. Cl.
CPC .......... *A61B 17/00* (2013.01); *A61B 17/1155* (2013.01); *A61B 2017/0046* (2013.01); *A61B 2017/00411* (2013.01)

(58) Field of Classification Search
CPC .......... A61B 17/00; A61B 2017/00017; A61B 2017/00367; A61B 2017/00411; A61B 2017/0046; A61B 17/00234; A61B 17/115; A61B 17/1155
USPC ...................................... 606/1, 130
See application file for complete search history.

(56) References Cited

U.S. PATENT DOCUMENTS

| | | | |
|---|---|---|---|
| 2,777,340 A | 1/1957 | Hettwer et al. |
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |

(Continued)

FOREIGN PATENT DOCUMENTS

| | | |
|---|---|---|
| CA | 2451558 A1 | 1/2003 |
| CN | 1547454 A | 11/2004 |

(Continued)

OTHER PUBLICATIONS

Extended European Search Report corresponding to International Application No. EP 14 18 4882.0 dated May 12, 2015.

(Continued)

*Primary Examiner* — Ahmed M Farah
(74) *Attorney, Agent, or Firm* — Carter, DeLuca & Farrell LLP (57) ABSTRACT

An adapter assembly, for connecting a surgical device to an electromechanical handle assembly, includes a cavity and a seal. The cavity is configured to receive a pin connector assembly of an electrical assembly of the electromechanical handle assembly. The seal is disposed at least partially within the cavity and is configured to reduce an amount of fluid able to contact the electrical assembly of the electromechanical handle assembly.

16 Claims, 10 Drawing Sheets

(56) References Cited

U.S. PATENT DOCUMENTS

| | | |
|---|---|---|
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,372,420 A | 12/1994 | Van Deursen et al. |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |

(56) References Cited

U.S. PATENT DOCUMENTS

| | | |
|---|---|---|
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,403,949 B2 | 3/2013 | Palmer et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 10,090,616 B1 | 10/2018 | Leimbach et al. |
| 10,667,408 B2 * | 5/2020 | Sgroi, Jr. ............... H05K 5/062 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |

(56) References Cited

U.S. PATENT DOCUMENTS

| | | |
|---|---|---|
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1* | 6/2015 | Zergiebel ............... H01R 39/08 227/175.1 |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2016/0310134 A1* | 10/2016 | Contini ............ A61B 17/07207 |
| 2018/0042689 A1* | 2/2018 | Mozdzierz ......... A61B 17/1155 |
| 2018/0360460 A1 | 12/2018 | Mozdzierz et al. |
| 2021/0128153 A1* | 5/2021 | Sgroi .................... A61B 90/98 |

FOREIGN PATENT DOCUMENTS

| | | |
|---|---|---|
| CN | 1957854 A | 5/2007 |
| CN | 101495046 A | 7/2009 |
| CN | 101856251 A | 10/2010 |
| CN | 102247182 A | 11/2011 |
| CN | 105682573 A | 6/2016 |
| DE | 102008053842 A1 | 5/2010 |
| EP | 0705571 A1 | 4/1996 |
| EP | 1563793 A1 | 8/2005 |

(56) References Cited

FOREIGN PATENT DOCUMENTS

| | | |
|---|---|---|
| EP | 1759652 A2 | 3/2007 |
| EP | 1769754 A1 | 4/2007 |
| EP | 1908412 A2 | 4/2008 |
| EP | 1917929 A1 | 5/2008 |
| EP | 1952769 A2 | 8/2008 |
| EP | 2090247 A1 | 8/2009 |
| EP | 2245994 A1 | 11/2010 |
| EP | 2316345 A1 | 5/2011 |
| EP | 2377472 A1 | 10/2011 |
| EP | 2668910 A2 | 12/2013 |
| EP | 2815705 A1 | 12/2014 |
| ES | 2333509 A1 | 2/2010 |
| FR | 2861574 A1 | 5/2005 |
| JP | 2005125075 A | 5/2005 |
| KR | 20120022521 A | 3/2012 |
| WO | 2011108840 A2 | 9/2011 |
| WO | 2012/040984 A1 | 4/2012 |

OTHER PUBLICATIONS

Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.
Notification of Transmittal of the International Search Report and The Written Opinion of the International Searching Authority issued in corresponding application No. PCT/US2016/027042 dated Jul. 12, 2016.
Extended European Search Report dated Mar. 9, 2020 corresponding to counterpart Patent Application EP 19205952.5.
European Office Action dated Mar. 9, 2020 corresponding to counterpart Patent Application EP 19205952.5.

* cited by examiner

SURGICAL DEVICES INCLUDING ADAPTERS AND SEALS

CROSS-REFERENCE TO RELATED APPLICATIONS

This application claims the benefit of and priority to U.S. Provisional Patent Application Ser. No. 62/752,550 filed Oct. 30, 2018, the entire disclosure of which is incorporated by reference herein.

BACKGROUND

1. Technical Field

The present disclosure relates to powered surgical devices. More specifically, the present disclosure relates to reusable handheld electromechanical surgical devices including adapters and seals.

2. Background of Related Art

Circular stapling instruments for performing surgical procedures such as anastomoses, hemorrhoidectomies, and mucosectomies are well known. These devices include an anvil assembly having a center rod and an anvil head supported on the center rod. The center rod of the anvil assembly is attachable to a trocar of the circular stapling instrument which enable linear translation of the anvil assembly. Typically, during a surgical procedure, the tool assembly of the circular stapling instrument is inserted into a tubular section or sections of tissue to join the tissue sections or remove diseased or damaged tissue from within the tissue section.

Additionally, various electrical components are typically used to enable communication between various components of the electromechanical surgical device. Keeping these electrical components free from contact with fluid (e.g., bodily fluid, insufflation fluid, etc.) is often helpful to maintain accurate and efficient communication between the electrical components, for example.

Accordingly, in view thereof, it is desirable to provide a seal to help prevent fluid from contacting electrical components of the adapter and surgical device.

SUMMARY

In accordance with aspects of the present disclosure, an adapter assembly for connecting a surgical device to an electromechanical handle assembly is provided. The adapter assembly includes a cavity and a seal. The cavity is configured to receive a pin connector assembly of an electrical assembly of the electromechanical handle assembly. The seal is disposed at least partially within the cavity and is configured to reduce an amount of fluid able to contact the electrical assembly of the electromechanical handle assembly.

The seal may be selectively positionable at least partially within the cavity.

In disclosed embodiments, the seal extends entirely through the cavity.

In embodiments, the seal includes a proximal rectangular ring and a distal rectangular ring. The proximal rectangular ring may define a larger perimeter than the distal rectangular ring. The seal may include a step interconnecting the proximal rectangular ring and the distal rectangular ring. The proximal rectangular ring may include a smaller longitudinal length than the distal rectangular ring.

In disclosed embodiments, at least a portion of the seal or an entirety of the seal is made from silicone.

A portion of the seal may extend proximally beyond a proximal edge of the cavity. A portion of the seal may extend distally beyond a distal edge of the cavity.

BRIEF DESCRIPTION OF THE DRAWINGS

Embodiments of the present disclosure are described herein with reference to the accompanying drawings, wherein.

DETAILED DESCRIPTION OF EMBODIMENTS

Embodiments of the present disclosure are now described in detail with reference to the drawings, in which like reference numerals designate identical or corresponding elements in each of the several views. As used herein the term "proximal" refers to a portion of a surgical device, or component thereof, closer to the user, and the term "distal" refers to a portion of the surgical device, or component thereof, farther from the user.

Figure 1:
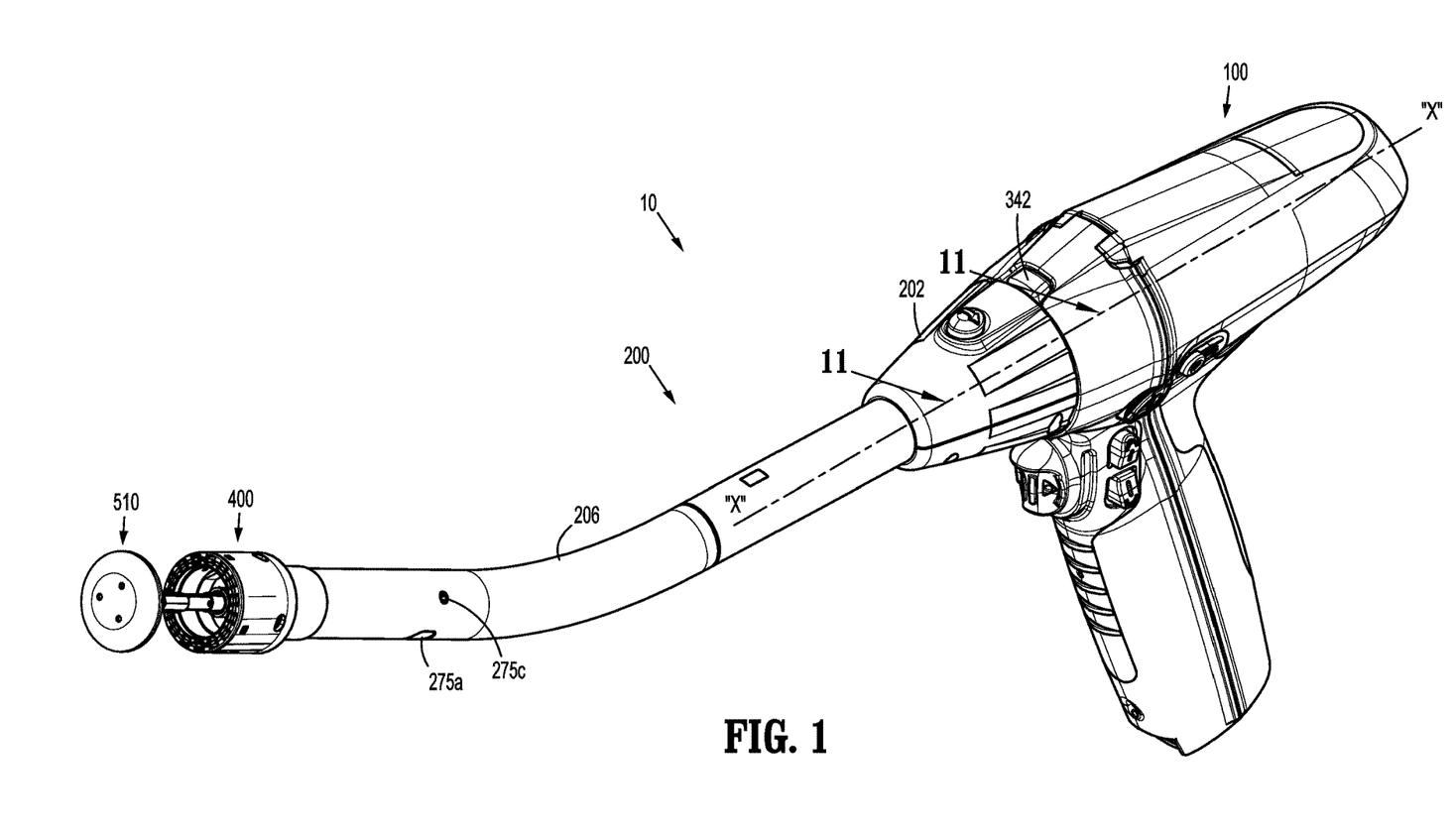
FIG. 1 is a perspective view of a handheld surgical device including a handle assembly, an adapter assembly, and a reload in accordance with an embodiment of the present disclosure.

Turning now to FIG. 1, a surgical device 10, in accordance with an embodiment of the present disclosure, is in the form of a powered handheld electromechanical instrument. The surgical device includes a handle assembly 100, an adapter assembly 200, a reload 400, and an anvil assembly 510. The handle assembly 100 is configured for selective connection with the adapter assembly 200 and, in turn, the adapter assembly 200 is configured for selective connection with the reload 400.

The handle assembly 100, the adapter assembly 200, and the reload 400 will only further be described to the extent necessary to disclose aspects of the present disclosure. For a detailed description of the structure and function of exemplary handle assemblies, adapter assemblies, and reloads, reference may be made to commonly owned U.S. Patent Appl. Pub. No. 2016/0310134 and U.S. patent application Ser. No. 15/972,606, the entire content of each of which is incorporated herein by reference.

Figure 2:
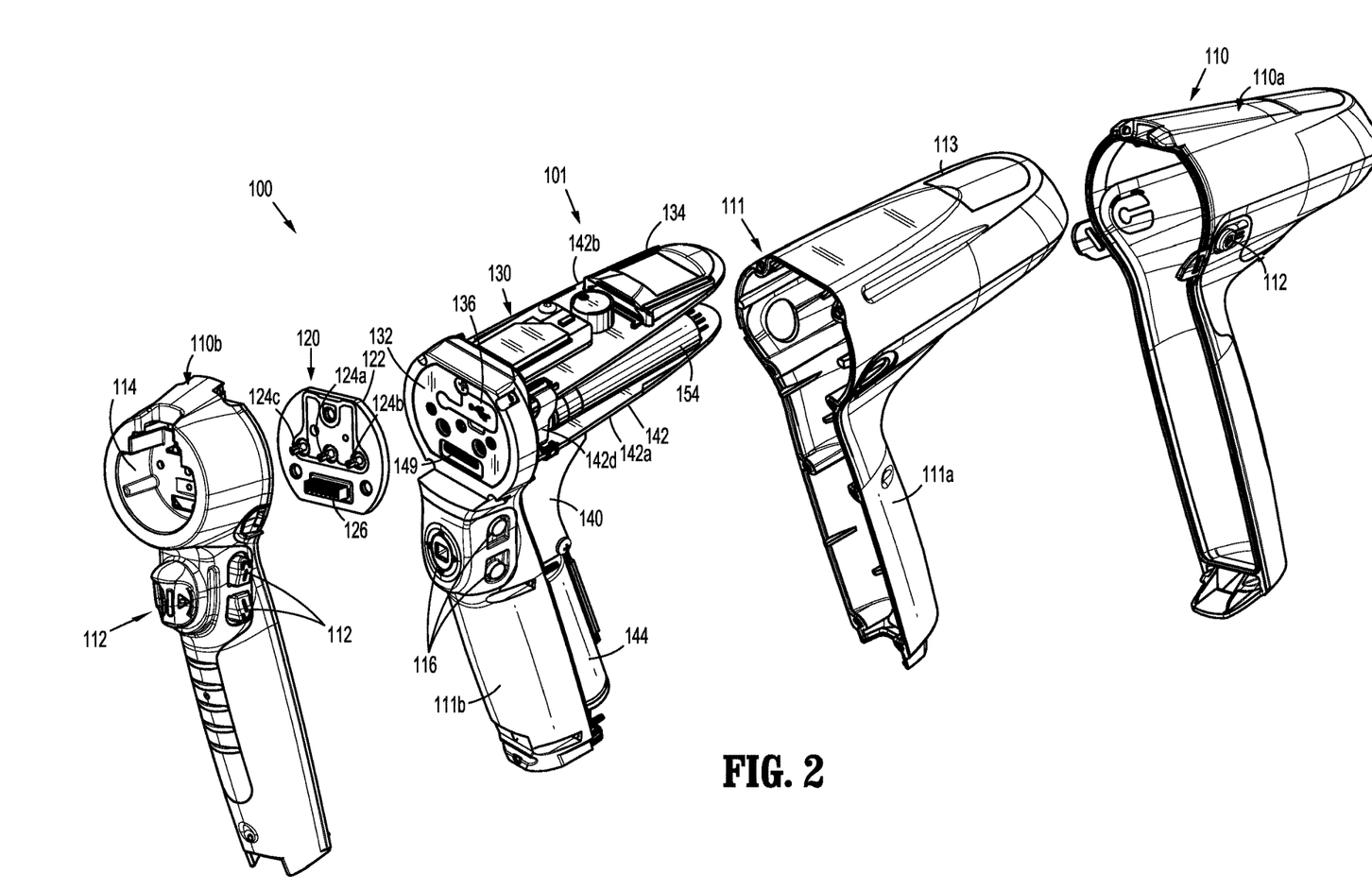
FIG. 2 is a perspective view, with parts separated, of the handle assembly of FIG. 1.

With reference now to FIG. 2, the handle assembly 100 includes a power handle 101 and an outer or shell housing 110 configured to selectively receive and encase the power handle 101. The shell housing 110 includes a proximal half-section 110a and a distal half-section 110b that are couplable together. The shell housing 110 includes a plurality of actuators 112 (e.g., finger-actuated control buttons, knobs, toggles, slides, interfaces, and the like) for activating various functions of the surgical device 10 (FIG. 1) upon application of a respective force thereto.

The distal half-section 110b of the shell housing 110 defines a connecting portion 114 (e.g., a recess) configured to accept or receive a corresponding drive coupling assembly 210 (FIG. 5) of the adapter assembly 200. A sterile barrier plate assembly 120 is selectively supported in the distal half-section 110b of the shell housing 110 behind the connection portion 114. The plate assembly 120 includes a plate 122 rotatably supporting three coupling shafts 124a, 124b, 124c, and having an electrical connector 126 supported thereon. The electrical connector 126 includes a chip and defines a plurality of contact paths each including an electrical conduit for extending an electrical connection across the plate 122. When the plate assembly 120 is disposed within the shell housing 110, distal ends of the coupling shafts 124a, 124b, 124c and the electrical connector 126 are disposed or situated within the connecting portion 114 of the shell housing 110 to electrically and/or mechanically engage respective corresponding features of the adapter assembly 200, as will be described in greater detail below.

The power handle 101 has an inner handle housing 111 including a proximal half section 111a and a distal half section 111b that are coupled together to house a power-pack core assembly 130 therein. The power-pack core assembly 130 is configured to control the various operations of the handle assembly 100 and thus, the surgical device 10.

The distal half section 111b of the inner handle housing 111 is configured and adapted to support a control plate 132 of the power-pack core assembly 130 such that the control plate 132 abuts the plate assembly 120 of the shell housing 110 when the power handle 101 is disposed within the shell housing 110. The distal half section 111b of the inner handle housing 111 also supports a plurality of actuator interfaces 116 that are in operative registration with the respective actuators 112 of the shell housing 110.

Figure 3:
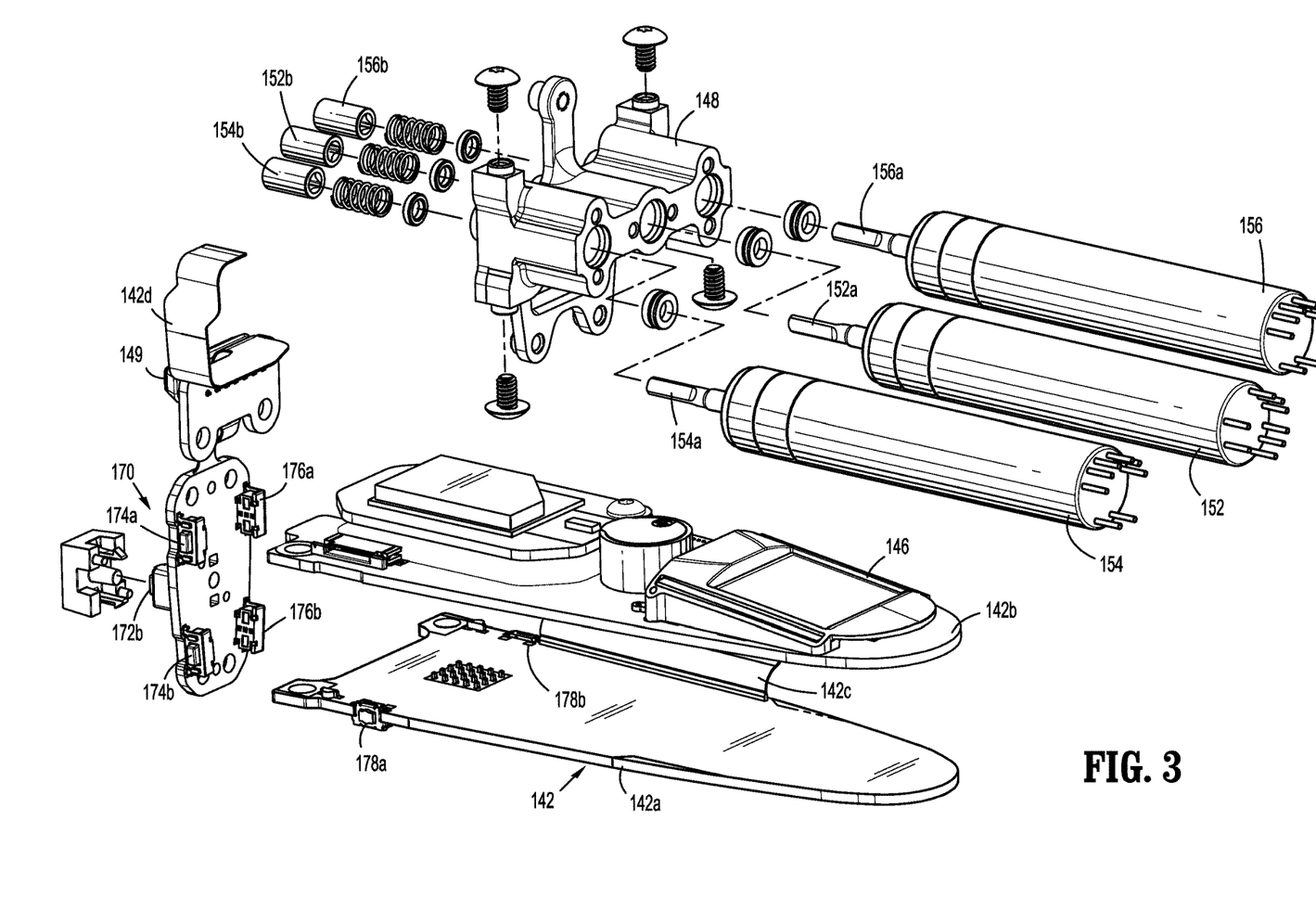
FIG. 3 is a perspective view, with parts separated, of a motor assembly and a control assembly of a power handle of the handle assembly of FIG. 2.

As shown in FIGS. 2 and 3, the power-pack core assembly 130 includes a battery circuit 140, a controller circuit board 142, and a rechargeable battery 144 configured to supply power to any of the electrical components of the handle assembly 100. The controller circuit board 142 includes a motor controller circuit board 142a, a main controller circuit board 142b, and a first ribbon cable 142c interconnecting the motor controller circuit board 142a and the main controller circuit board 142b. A display screen 134 is supported on the main controller circuit board 142b and visible through a clear or transparent window 113 provided in the proximal half-section 111a of the inner handle housing 111. A USB connector 136 (or other data connector) is also supported on the main controller circuit board 142b and is accessible through the control plate 132 of the power-pack core assembly 130.

The power-pack core assembly 130 further includes a first motor 152, a second motor 154, and a third motor 156 disposed between the motor controller circuit board 142a and the main controller circuit board 142b. Each of the first, second, and third motors 152, 154, 156 is electrically connected to the controller circuit board 142 and the battery 144, and controlled by a respective motor controller disposed on the motor controller circuit board 142a which, in turn, is coupled to a respective main controller disposed on the main controller circuit board 142b.

Each of the first, second, and third motors 152, 154, 156 is supported on a motor bracket 148 such that respective motor shaft 152a, 154a, 156a extending from the first, second, and third motors 152, 154, 156 are rotatably disposed within respective apertures of the motor bracket 148. The motor bracket 148 rotatably supports three rotatable drive connector sleeves 152b, 154b, 156b that are keyed to the respective motor shafts 152a, 154a, 156a of the first, second, and third motors 152, 154, 156. The drive connector sleeves 152b, 154b, 156b non-rotatably receive proximal ends of the respective coupling shafts 124a, 124b, 124c of the plate assembly 120 of the shell housing 110, when the power handle 101 is disposed within the shell housing 10, and are each spring biased away from the respective motors 152, 154, 156.

The motor bracket 148 also supports an electrical receptacle 149. The electrical receptacle 149 is in electrical connection with the main controller circuit board 142b by a second ribbon cable 142d. The electrical receptacle 149 defines a plurality of electrical slots for receiving respective electrical contacts or blades extending from the pass-through connector 126 of the plate assembly 120 of the shell housing 110.

Rotation of the motor shafts 152a, 154a, 156a by the respective first, second, and third motors 152, 154, 156 function to drive shafts and/or gear components of the adapter assembly 200 in order to perform the various operations of the handle assembly 100, as will be described in greater detail below.

In use, when the adapter assembly 200 is mated to the handle assembly 100, each of the coupling shafts 124a, 124b, 124c of the handle assembly 100 couples with a corresponding rotatable connector sleeve 218, 222, 220 (FIG. 6) of the adapter assembly 200. In this regard, the interface between corresponding coupling shafts 124a, 124b, 124c and connector sleeves 218, 222, 220 are keyed such that rotation of each of the coupling shafts 124a, 124b, 124c of the handle assembly 100 causes a corresponding rotation of the corresponding connector sleeve 218, 222, 220 of the adapter assembly 200.

The coupling shafts 124a, 124b, 124c of handle assembly 100 are configured to be independently rotated by the respective motor 152, 154, 156 such that rotational force(s) are selectively transferred from the motors 152, 154, 156 of the handle assembly 100 to the adapter assembly 200. The selective rotation of the coupling shaft(s) 124a, 124b, 124c of the handle assembly 100 allows the handle assembly 100 to selectively actuate different functions of the reload 400.

Figure 4:
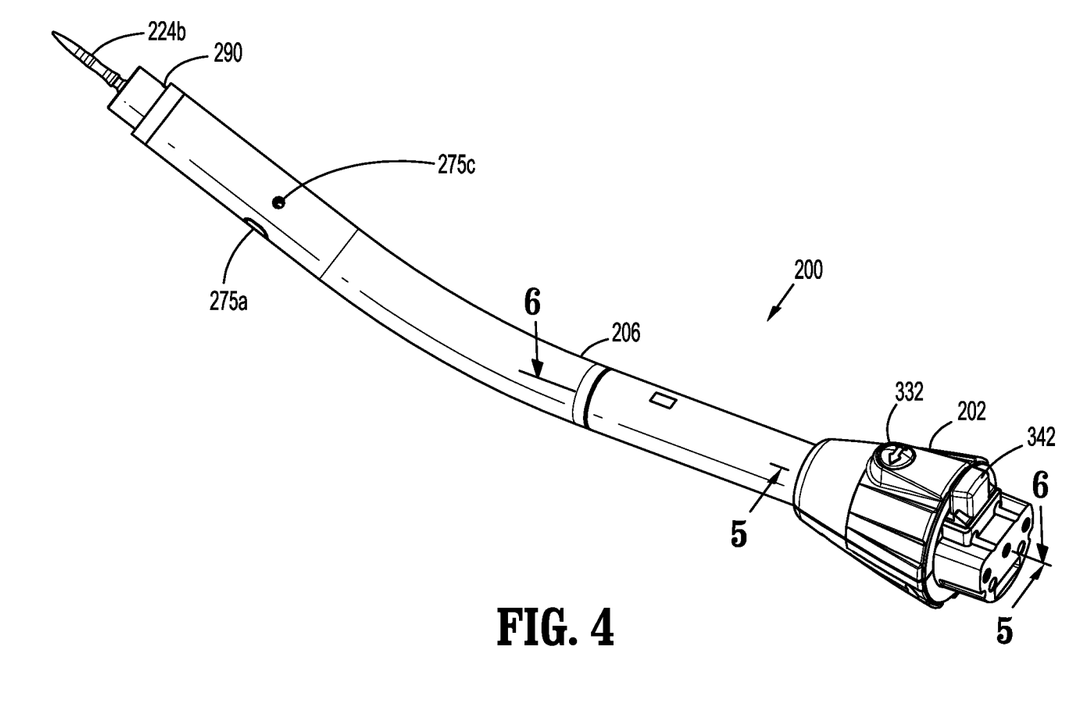
FIG. 4 is a perspective view of the adapter assembly without the reload secured to a distal end thereof.

Turning now to FIG. 4, the adapter assembly 200 is configured to convert a rotation of the coupling shaft(s) 124a, 124b, 124c (FIG. 2) of the handle assembly 100 into axial translation useful for effecting various functions of the surgical device 10 (FIG. 1). The adapter assembly 200 includes an adapter or knob housing 202 and an outer tube 206 extending from a distal end of the knob housing 202. The knob housing 202 and the outer tube 206 are configured and dimensioned to house and support the components of the adapter assembly 200. The knob housing 202 includes a drive coupling assembly 210 which is configured and adapted to connect to the connecting portion 114 (FIG. 2) of the shell housing 110 of the handle assembly 100. The outer tube 206 includes a connector sleeve 290 fixedly supported at a distal end thereof. The connector sleeve 290 is configured to selectively secure the reload 400 (FIG. 1) to the adapter assembly 200.

Figure 5:
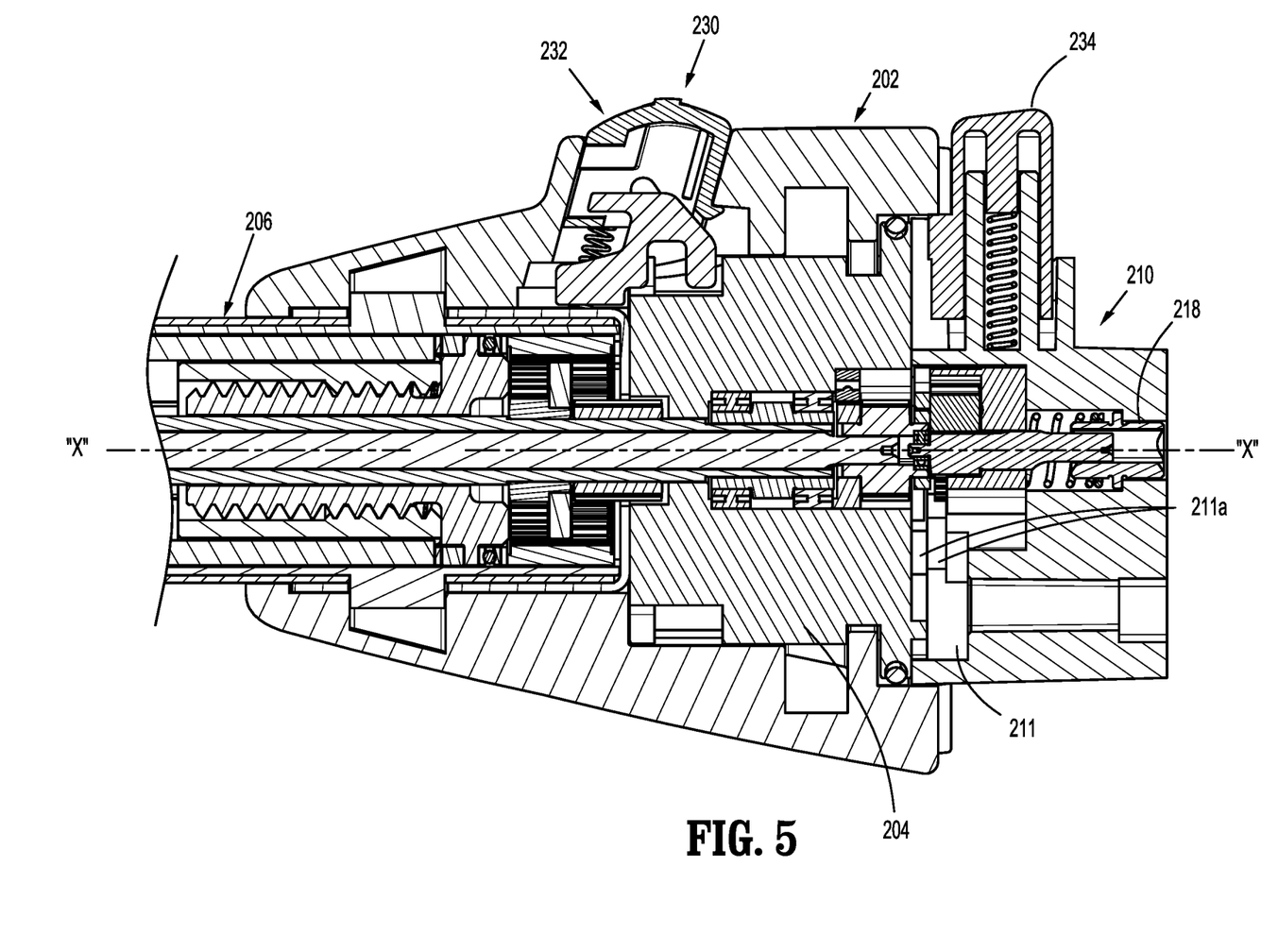
FIG. 5 is a cross-sectional view of the adapter assembly of FIG. 4, as taken through section line 5-5 of FIG. 4.

As shown in FIGS. 4 and 5, the adapter assembly 200 includes a rotation assembly 230 configured to enable rotation of the adapter assembly 200 relative to the handle assembly 100. Specifically, the knob housing 202 and the outer tube 206 of the adapter assembly 200 are rotatable relative to the drive coupling assembly 210 of the adapter assembly 200. The rotation assembly 230 includes a lock button 232 operably supported on the knob housing 202 and configured for actuating the rotation assembly 230. When rotation assembly 230 is in an unlocked configuration, the knob housing 202 and the outer tube 206 are rotatable along a longitudinal axis "X" of the adapter assembly 200 relative to the drive coupling assembly 210. When rotation assembly 230 is in a locked configuration, the knob housing 202 and the outer tube 206 are rotationally secured relative to the drive coupling assembly 210.

The adapter assembly 200 further includes an attachment/detachment button 234 supported on the drive coupling assembly 210 of the adapter assembly 200. In use, when the adapter assembly 200 is connected to the shell housing 110 of the handle assembly 100, the attachment/detachment button 234 secures and retains the adapter assembly 200 and the handle assembly 100 with one another. When the attachment/detachment button 234 is depressed or actuated, the adapter assembly 200 and the handle assembly 100 may be disconnected from each other.

The adapter assembly 200 further includes a cavity 211 defined within the drive coupling assembly 210 that is configured to receive a connector assembly 320 (FIG. 11) of an electrical assembly 300 configured for establishing an electrical connection with and between the handle assembly 100, the adapter assembly 200, and the reload 400, as described in further detail below. The cavity 211 may include guiding ribs 211a configured to receive a printed circuit board of the connector assembly 320.

Figure 6:
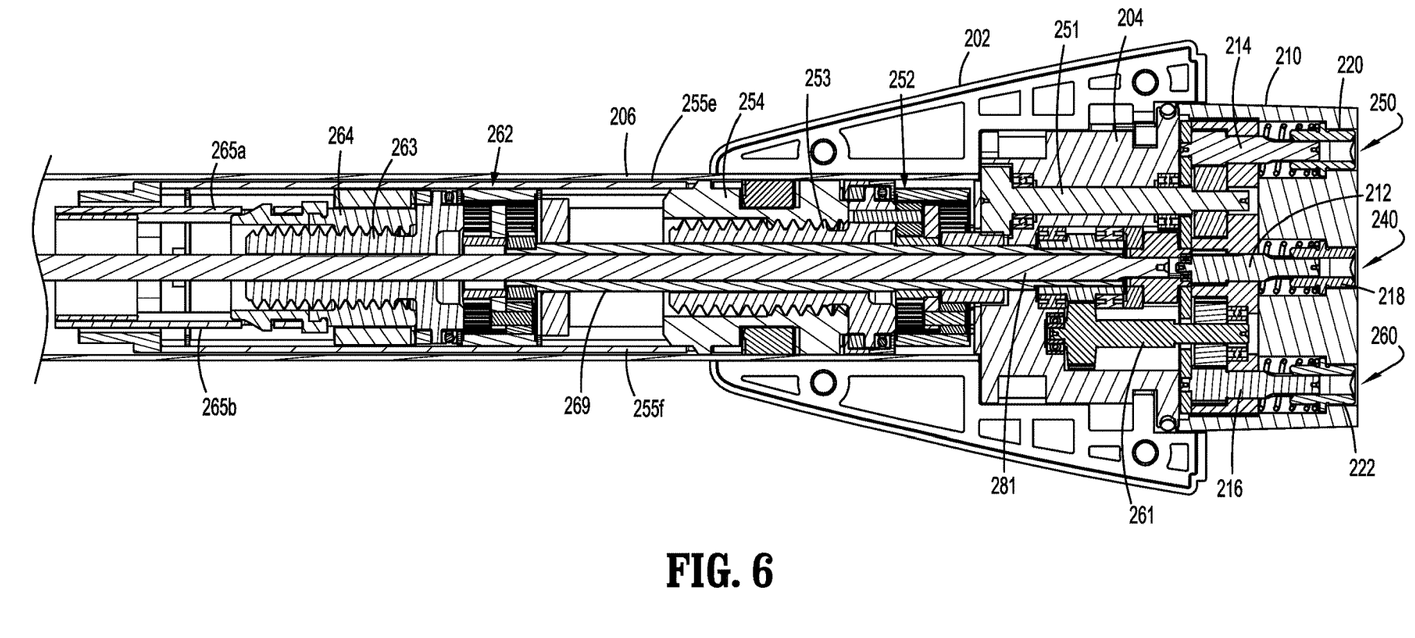
FIG. 6 is a cross-sectional view of the adapter assembly of FIG. 4, as taken through section line 6-6 of FIG. 4.

As illustrated in FIG. 6, the drive coupling assembly 210 of the adapter assembly 200 rotatably supports first, second, and third connector sleeves 218, 220 and 222 therein, and an inner housing member 204 disposed within the knob housing 202 rotatably supports first, second, and third rotatable proximal drive shafts 212, 214, 216 therein. Each of the first, second, and third connector sleeves 218, 220, 222 is configured to mate with a respective coupling shaft 124a, 124c, 124b (FIG. 2) of the handle assembly 100. Each of the first, second, and third connector sleeves 218, 220, 222 is further configured to mate with a proximal end of the respective first, second, and third proximal drive shafts 212, 214, 216 of the adapter assembly 200 such that each of the first, second, and third proximal drive shafts 212, 214, 216 functions as a rotation receiving member to receive rotational forces from the respective coupling shafts 124a, 124c, 124b of the handle assembly 100.

The adapter assembly 200 includes first, second and third force/rotation transmitting/converting assemblies 240, 250, 260 disposed within the inner housing member 204 and the outer tube 206. Each of the force/rotation transmitting/converting assemblies 240, 250, 260 is configured and adapted to transmit or convert a rotation of the respective coupling shaft 124a, 124c, 124b of the handle assembly 100 into axial translation to effectuate operation of the reload 400 (FIG. 1), as will be described in greater detail below.

Referring now to FIGS. 7-11, a seal 500, for use with and/or between adapter assembly 200 and handle assembly 100, is shown. Seal 500 is positioned at least partially within cavity 211 of drive coupling assembly 210 of adapter assembly 200 and is configured to prevent or limit fluid from entering electrical receptacle 149 of handle assembly 100. More particularly, seal 500 is configured to help prevent fluid from travelling between adapter assembly 200 and handle assembly 100, to thereby help prevent the fluid from interfering with the electrical components thereof and connections therebetween. Seal 500 may be provided as an integral part of adapter assembly 200, or may be provided as a separate add on accessory or component to adapter assembly 200.

With particular reference to FIGS. 8-11, seal 500 includes a proximal portion 510, a distal portion 520, and a step 530 disposed between and interconnecting proximal portion 510 and distal portion 520. Proximal portion 510 includes four walls generally defining an open rectangular prism or rectangular ring, and distal portion 520 includes four walls generally defining an open rectangular prism or rectangular ring. In embodiments, seal 500 includes a distal lip disposed on or adjacent a distal edge of distal portion 520 and includes a larger perimeter than distal portion 520.

Figure 10:
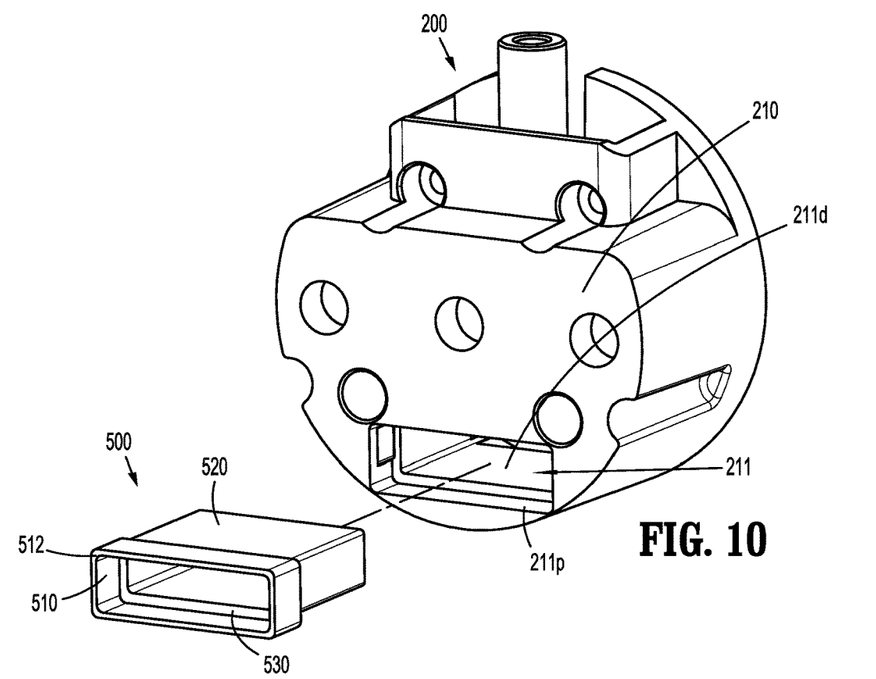
FIG. 10 is a perspective view, with parts separated, of the adapter assembly and seal of FIGS. 7-9.

As shown in FIG. 10, a perimeter of the space defined by proximal portion 510 of seal 500 is larger than a perimeter of the space defined by distal portion 520 of seal 500. FIG. 10 also shows that a length of proximal portion 510 of seal 500 is smaller than a length of distal portion 520 of seal 500. While the relative sizes of the perimeters and lengths of proximal portion 510 and distal portion 520 are shown to accommodate the dimensions of cavity 211 of drive coupling assembly 210 of adapter assembly 200 shown, other sizes and shapes of proximal portion 510 and distal portion 520 of seal 500 are contemplated by the present disclosure.

Figure 7:
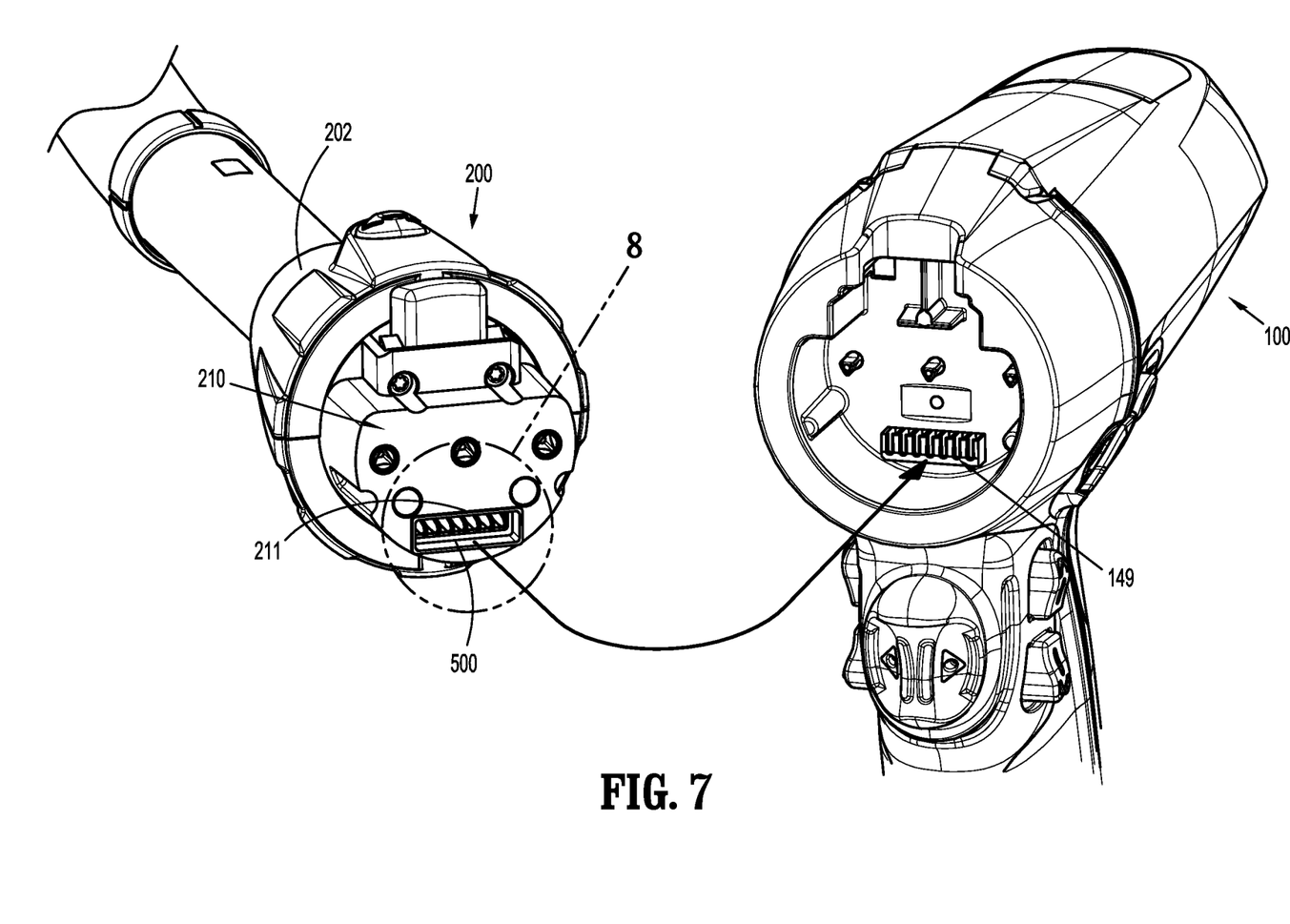
FIG. 7 is an assembly view of portions of the handheld surgical device of FIG. 1 illustrating the adapter assembly including a seal and being separated from the electromechanical handle assembly.
Figure 8:
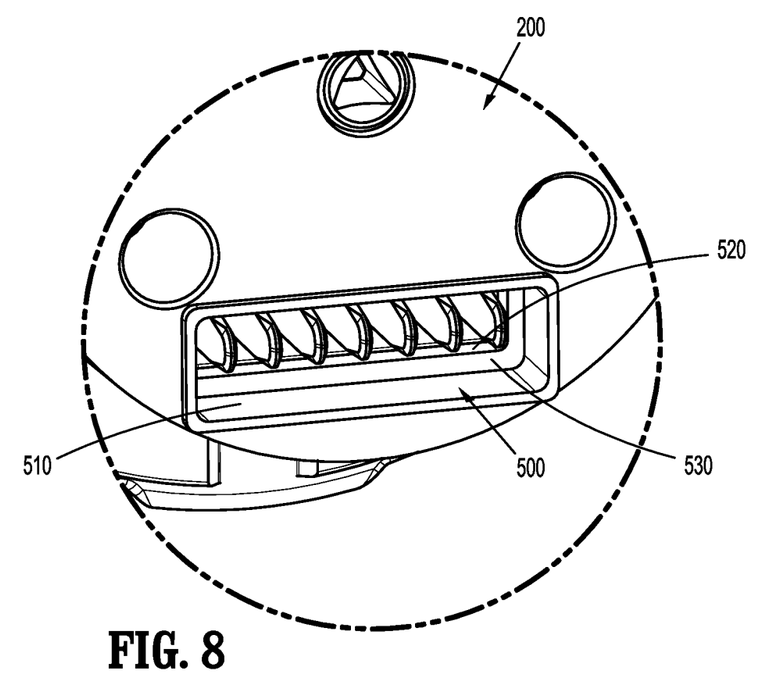
FIG. 8 is an enlarged view of the indicated area of detail of FIG. 7 illustrating the seal of the adapter assembly.
Figure 9:
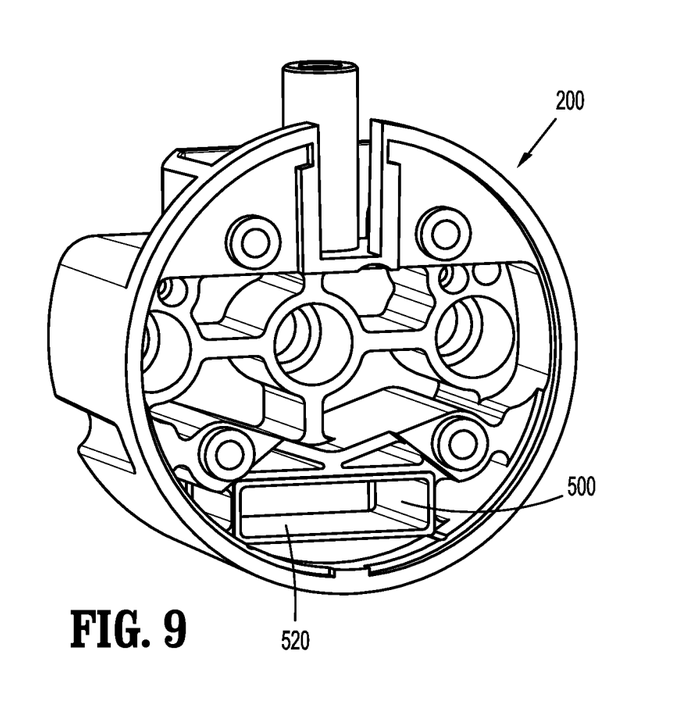
FIG. 9 is a perspective view of a portion of the adapter assembly illustrating the seal of FIGS. 7 and 8.

Seal 500 is made from silicone or another material (or materials) suitable for providing a waterproof or essentially waterproof barrier. Additionally, the material of seal 500 may enable seal 500 to deflect, which may facilitate positioning of seal 500 at least partially within cavity 211 of drive coupling assembly 210 of adapter assembly 200. Furthermore, the compressibility of seal 500 allows a proximal edge 512 of proximal portion 510 of seal 500 to extend from cavity 211, such that proximal edge 512 is able to compress upon engagement between adapter assembly 200 and handle assembly 100, thereby resulting in a robust fluid-tight seal between adapter assembly 200 and handle assembly 100. Additionally, the compressibility of seal 500 helps ensure a robust fluid-tight seal between adapter assembly 200 and portions of knob housing 202 (FIGS. 5 and 7).

Figure 11:
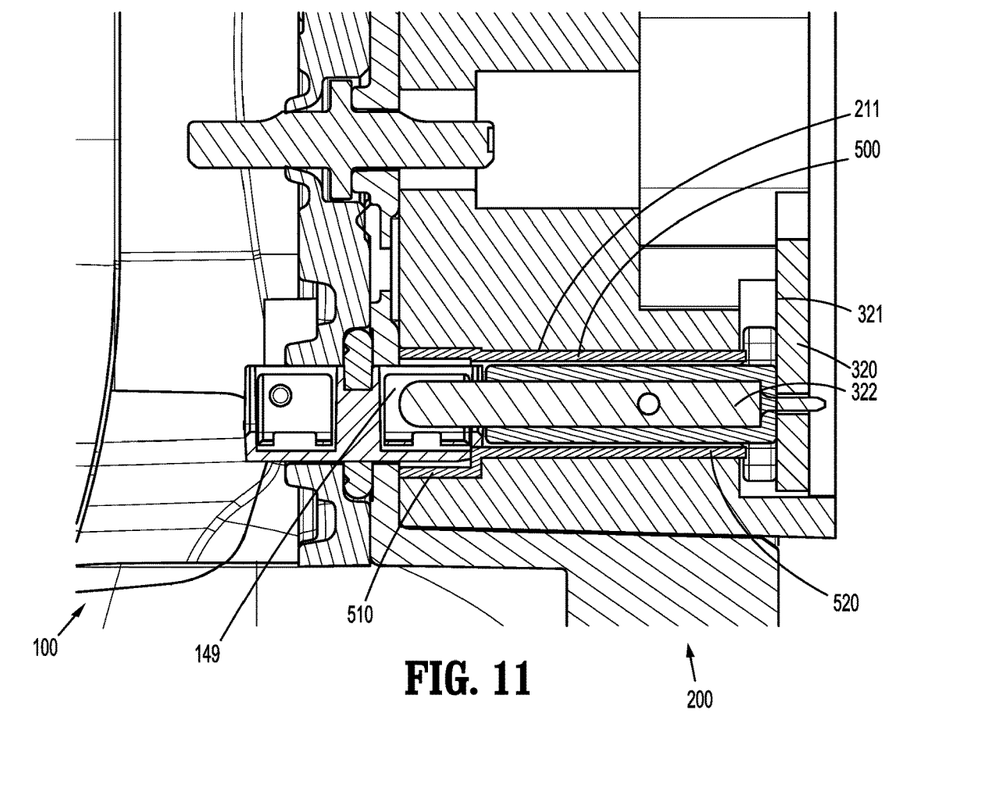
FIG. 11 is a cross-sectional view as taken through 11-11 of FIG. 1.

With reference to FIGS. 10 and 11, seal 500 is substantially positioned within cavity 211 of drive coupling assembly 210 of adapter assembly 200. More particularly, a majority of proximal portion 510 of seal 500 is positioned within a proximal portion 211p of cavity 211, and distal portion 520 of seal 500 is positioned within a distal portion 211d of cavity 211 (FIG. 10). As noted above, proximal edge 512 of proximal portion 510 of seal 500 may extend proximally beyond a proximal edge of cavity 211 to help ensure a robust seal between adapter assembly 200 and handle assembly 100. Further, when adapter assembly 200 is engaged with handle assembly 100, proximal portion 510 of seal 500 is configured to surround or encircle a portion (e.g., a distal portion) of electrical receptacle 149 of handle assembly 100 and is configured to surround or encircle a proximal portion of pins 322 of connector assembly 320 within or extending at least partially through adapter assembly 200 (FIG. 11). Distal portion 520 of seal 500 is configured to encircle a portion (e.g., a distal portion) of pins 322 of connector assembly 320. A distal edge or lip of seal 500 may be compressed between a distal edge of cavity 211 and a proximal wall 321 of connector assembly 320.

Additionally, portions of connector assembly 320 that are not protected by seal 500 may be coated with a waterproofing material to help protect those components from fluid and moisture.

Accordingly, seal 500 helps prevent or limit fluid from entering cavity 211 of drive coupling assembly 210 of adapter assembly 200, helps prevent or limit fluid from contacting electrical components of connector assembly 320 within or extending through cavity 211, and helps prevent or limit fluid from entering electrical receptacle 149 of handle assembly 100. Seal 500 thereby helps ensure proper electrical communication between handle assembly 100 and adapter assembly 200.

With reference to FIGS. 1-6, in operation, the first force/rotation transmitting/converting assembly 240 functions to advance/retract trocar member 274 of trocar assembly 270 of the adapter assembly 200, and to open/close the reload 400 (FIG. 1) when an anvil assembly 510 is connected to the trocar member 274. Specifically, as the first rotatable proximal drive shaft 212 is rotated, due to a rotation of the first connector sleeve 218, as a result of the rotation of the first coupling shaft 124a (FIG. 2) of the handle assembly 100, the second rotatable proximal drive shaft 281 is caused to be rotated. Rotation of the second rotatable proximal drive shaft 281 results in contemporaneous rotation of the rotatable distal drive shaft 282. Rotation of the rotatable distal drive shaft 282 causes contemporaneous rotation of the coupling member 286, which, in turn, causes contemporaneous rotation of the drive screw 276 of the trocar assembly 270. As the drive screw 276 is rotated within and relative to the trocar member 274, engagement between the trocar member 274 and the drive screw 276 (e.g., threaded engagement) causes axial translation of the trocar member 274 within the tubular housing 272 of the trocar assembly 270. Specifically, rotation of the drive screw 276 in a first direction causes axial translation of the trocar member 274 in a first direction (e.g., extension or advancement of the trocar assembly 270), and rotation of the drive screw 276 in a second direction causes axial translation of the trocar member 274 in a second direction (e.g., retraction of the trocar assembly 270). When the anvil assembly 510 is connected to the trocar member 274, the axial translation of the trocar member 274 in the first direction results in an opening of the reload 400, and the axial translation of the trocar member 274 in the second direction results in a closing of the reload 400.

Figures 12, 13:
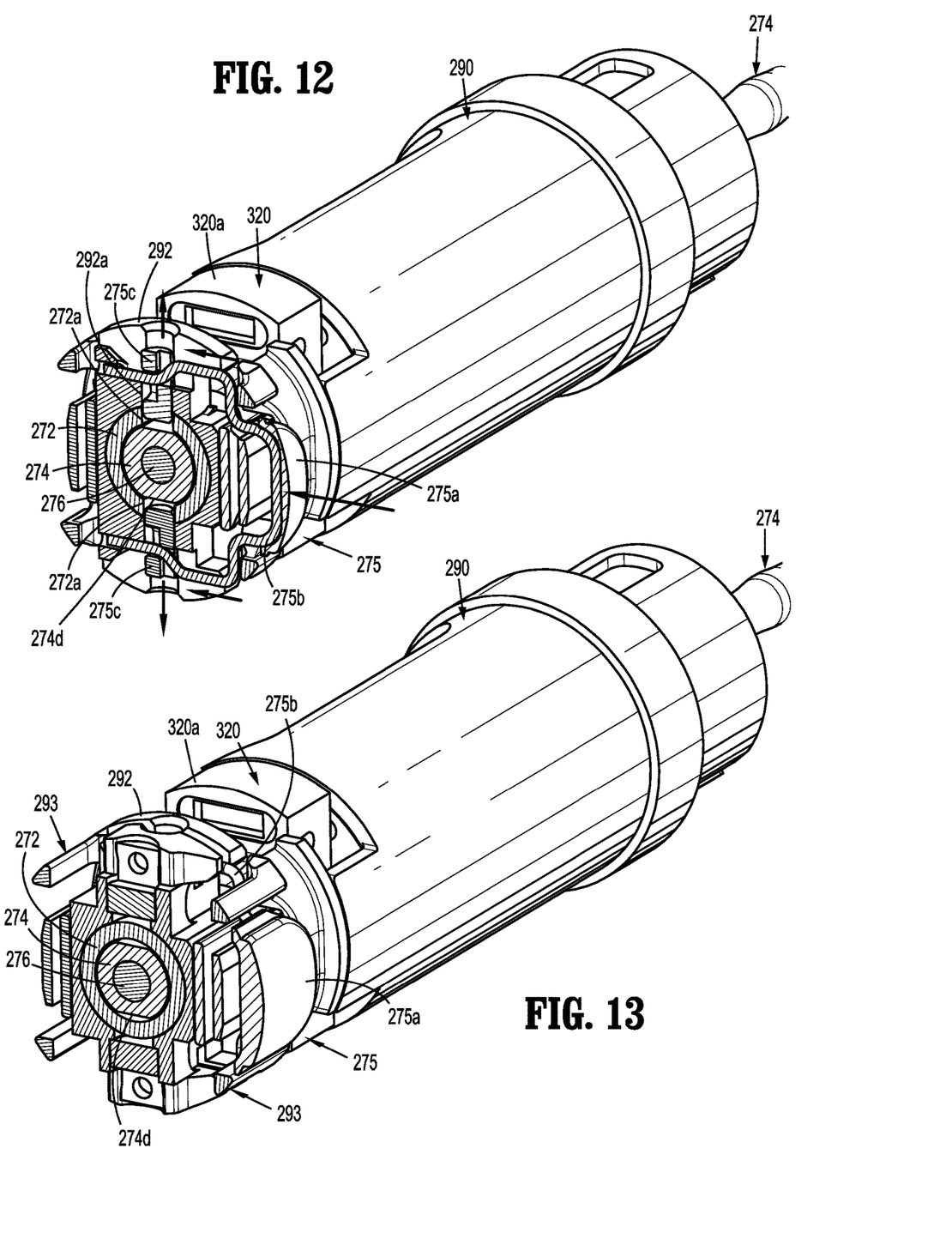
FIG. 12 is a perspective view of the adapter assembly of FIG. 4, shown partially in phantom, illustrating a second force/rotation transmitting/converting assembly thereof.
FIG. 13 is a perspective view of the adapter assembly of FIG. 4, shown partially in phantom, illustrating a third force/rotation transmitting/converting assembly thereof.

As shown in FIG. 6, the second force/rotation transmitting/converting assembly 250 of adapter assembly 200 includes the second proximal drive shaft 214, as described above, a first coupling shaft 251, a planetary gear set 252, a staple lead screw 253, and a staple driver 254. The second force/rotation transmitting/converting assembly 250 of the adapter assembly 200 also includes an outer flexible band assembly 255 secured to the staple driver 254. The outer flexible band assembly 255 includes first and second flexible bands 255a, 255b laterally spaced and connected at proximal ends thereof to a support ring 255c and at distal ends thereof to a proximal end of a support base 255d. The outer flexible band assembly 255 further includes first and second connection extensions 255e, 255f extending proximally from the support ring 255c that are configured to operably connect the outer flexible band assembly 255 to the staple driver 254. The second force/rotation transmitting/converting assembly 250 functions to fire staples "S" (FIG. 13) of the reload 400 for formation against the anvil assembly 510.

In operation, as the second rotatable proximal drive shaft 214 is rotated due to a rotation of the second connector sleeve 220, as a result of the rotation of the second coupling shaft 124c (FIG. 2) of the handle assembly 100, the first coupling shaft 251 is caused to be rotated, which in turn causes the planetary gear set 252 to rotate. Rotation of the planetary gear set 252 causes contemporaneous rotation of the staple lead screw 253. As the staple lead screw 253 is rotated, the staple driver 254 is caused to be axially translated, which in turn causes the outer flexible band assembly 255 to be axially translated. As the outer flexible band assembly 255 is axially translated, the support base 255d presses against a driver adapter of a staple driver assembly (not shown) of the reload 400 to distally advance a driver and fire staples from a staple cartridge (not shown) of the reload 400 and against anvil assembly 510 for formation of the staples in underlying tissue.

With reference to FIG. 6, the third force/rotation transmitting/converting assembly 260 of the adapter assembly 200 includes the third proximal drive shaft 216, as described above, a second coupling shaft 261, a hollow shaft 269, a planetary gear set 262, a knife lead screw 263, and a knife driver 264. The third force/rotation transmitting/converting assembly 260 of adapter assembly 200 also includes an inner flexible band assembly 265 secured to the knife driver 264. The inner flexible band assembly 265 includes first and second flexible bands 265a, 265b laterally spaced and connected at proximal ends thereof to a support ring 265c and at distal ends thereof to a proximal end of a support base 265d. The third force/rotation transmitting/converting assembly 260 functions to fire an annular knife of the reload 400.

In operation, as the third rotatable proximal drive shaft 216 is rotated due to a rotation of the third connector sleeve 222, as a result of the rotation of the third coupling shaft 124b (FIG. 2) of the handle assembly 100, the second coupling shaft 261 is caused to be rotated, which in turn causes the hollow shaft 269 to rotate. Rotation of the hollow shaft 269 results in contemporaneous rotation of the planetary gear set 262, which in turn causes the knife lead screw 263 to rotate. As the knife lead screw 263 is rotated, the knife driver 264 is caused to be axially translated, which in turn causes the inner flexible band assembly 265 to be axially translated. As the inner flexible band assembly 265 is axially translated, the support base 265d presses against a knife carrier (not shown) of the reload 400 to distally advance the knife carrier and fire the an annular knife (not shown) of the reload 400 against the anvil assembly 510 for cutting of tissue clamped in the reload 400.

Persons skilled in the art will understand that the structures specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. For example, the electrical assemblies of the present disclosure may be configured for use with a plurality of different reloads via a plurality of respective adapter assemblies that are each configured for actuation and manipulation by a powered handle assembly and/or a robotic surgical system. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An adapter assembly for connecting a surgical device to an electromechanical handle assembly and configured to convert rotation of shafts of the electromechanical handle assembly to axial translation for effecting various functions of the surgical device, the adapter assembly comprising:
   a cavity configured to receive a connector assembly of an electrical assembly of the electromechanical handle assembly; and
   a seal disposed at least partially within the cavity and configured to reduce an amount of fluid able to contact the electrical assembly of the electromechanical handle assembly.

2. The adapter assembly according to claim 1, wherein the seal is selectively positionable at least partially within the cavity.

3. The adapter assembly according to claim 1, wherein the seal extends entirely through the cavity.

4. The adapter assembly according to claim 1, wherein the seal includes a proximal rectangular ring and a distal rectangular ring.

5. The adapter assembly according to claim 4, wherein the proximal rectangular ring defines a larger perimeter than the distal rectangular ring.

6. The adapter assembly according to claim 4, wherein the seal includes a step interconnecting the proximal rectangular ring and the distal rectangular ring.

7. The adapter assembly according to claim 4, wherein the proximal rectangular ring includes a smaller longitudinal length than the distal rectangular ring.

8. The adapter assembly according to claim 1, wherein at least a portion of the seal is made from silicone.

9. The adapter assembly according to claim 1, wherein an entirety of the seal is made from silicone.

10. The adapter assembly according to claim 1, wherein a portion of the seal extends proximally beyond a proximal edge of the cavity.

11. The adapter assembly according to claim 1, wherein a portion of the seal extends distally beyond a distal edge of the cavity.

12. The adapter assembly according to claim 1, wherein the seal includes a proximal rectangular ring.

13. The adapter assembly according to claim 1, wherein the seal includes a distal rectangular ring.

14. The adapter assembly according to claim 1, wherein the seal includes a proximal ring.

15. The adapter assembly according to claim 1, wherein the seal includes a distal ring.

16. The adapter assembly according to claim 1, wherein the seal includes a proximal ring and a distal ring.

* * * * *